United States Patent [19]

Barradas

[11] Patent Number: 5,735,918
[45] Date of Patent: Apr. 7, 1998

[54] COMBINATION AIR FRESHENER AND AIR FILTER

[76] Inventor: George Barradas, 15 River View Ct., Greenwich, Conn. 06831

[21] Appl. No.: 752,251

[22] Filed: Nov. 19, 1996

[51] Int. Cl.$^6$ .................................................. B01D 35/14
[52] U.S. Cl. .......................... 55/274; 55/279; 55/385.1; 55/486; 55/521; 422/124
[58] Field of Search .................. 55/126, 279, 490, 55/484, 493, 385.1, 385.2, 508, 511, 497, 521, 486, 270, 274; 96/148, 57; 362/226; 422/116; 261/104, 107, DIG. 17, DIG. 65

[56] References Cited

U.S. PATENT DOCUMENTS

| | | | |
|---|---|---|---|
| 2,992,701 | 7/1961 | White | 55/508 |
| 3,744,216 | 7/1973 | Halloran | 422/124 X |
| 3,807,148 | 4/1974 | Fike et al. | 55/446 |
| 4,064,203 | 12/1977 | Cox | 55/473 |
| 4,252,547 | 2/1981 | Johnson | 55/484 |
| 4,597,781 | 7/1986 | Spector | 96/52 |
| 4,695,434 | 9/1987 | Spector | 422/116 |
| 4,816,973 | 3/1989 | Atalla et al. | 362/226 |
| 5,181,883 | 1/1993 | Hofstra et al. | 55/385.2 |
| 5,186,903 | 2/1993 | Cornwell | 422/122 |

FOREIGN PATENT DOCUMENTS

| | | | |
|---|---|---|---|
| 0197218 | 10/1985 | Japan | 55/490 |
| 404200608A | 7/1992 | Japan | 55/490 |
| 405031313A | 2/1993 | Japan | 55/490 |

*Primary Examiner*—Richard L. Chiesa
*Attorney, Agent, or Firm*—Alfred E. Miller

[57] ABSTRACT

An automatically operating air filter and air freshener device which can be mounted on a wall or is self supporting, and in which the motor fan unit is located in front of the filters and part of the air flow is directed to pass through a scent element, while the remainder of the air flow passes through an exit opening in the rear of the device spaced from the wall.

15 Claims, 6 Drawing Sheets

COMBINATION AIR FRESHENER AND AIR FILTER

The present invention relates to a room unit for aromatically freshening the air in the room while simultaneously filtering the room air when a person enters the room. The unit can stay in operation for a pre-determined period after the person leaves the room.

Air fresheners are known which generate pleasant aromas in rooms likely to have occasional odors, such as bathrooms, kitchens and work places. An example of an aroma generating unit is found in U.S. Pat. No. 4,695,434. Air purifier devices are seen in U.S. Pat. No. 3,744,216 and U.S. Pat. No. 4,597,781. In the later patent a volatized aromatic liquid is used to import a fragrance in a room. In U.S. Pat. No. 5,186,903 an apparatus is shown for purifying indoor air by first passing indoor air through a series of filters by means of blower and exiting through an outlet of the apparatus.

SUMMARY OF THE INVENTION

The present invention overcomes the disadvantages of the prior art construction by having a motor fan immediately adjacent to the inlet to the device so that inlet air is sucked into the device before contacting the filters thus causes air to pass through the filter arrangement at a greater velocity than the case where the blower is located behind a whole series of filters.

It is an object of the present invention to provide a portable air treatment device for both the air in a room as well as removing noxious odors therein.

It is a feature of the present invention to pass the incoming room air through filters in series and then branch out part of the filtered air through an aroma generating substance and into the room while the remaining filtered air exists directly into the room, thus propelling both filtered air and freshened or scented air simultaneously in a room.

It is an object of the present invention to provide a first filter of foam for separating out large particles present in the room air and secondary filter for smaller particles having a sinuous configuration in order to present a larger surface for filtering the particles still in the room air that pass through the filters.

It is another feature of the present invention to provide a combination air freshener and air filter as a single compact unit provided with means for mounting the unit to a wall, as well as having the capability of being free-standing.

It is another object of the present invention to provide a scent container that is removably mounted in a well in the top of the unit; and has both top and bottom openings for the passage of filtered air therethrough.

A further feature of the present invention is to provide a sensor for the portable air treatment device which becomes activated upon movement of an individual in the vicinity of the device.

Another object of the present invention is to provide a delay timer which can be selectively used to continue the activation of the air treatment device after an individual has left the room or the immediate vicinity.

The above and other objects and features of the invention will be apparent by reference to the following description of my invention and drawings.

DESCRIPTION OF THE PREFERRED EMBODIMENT

Figure 3:
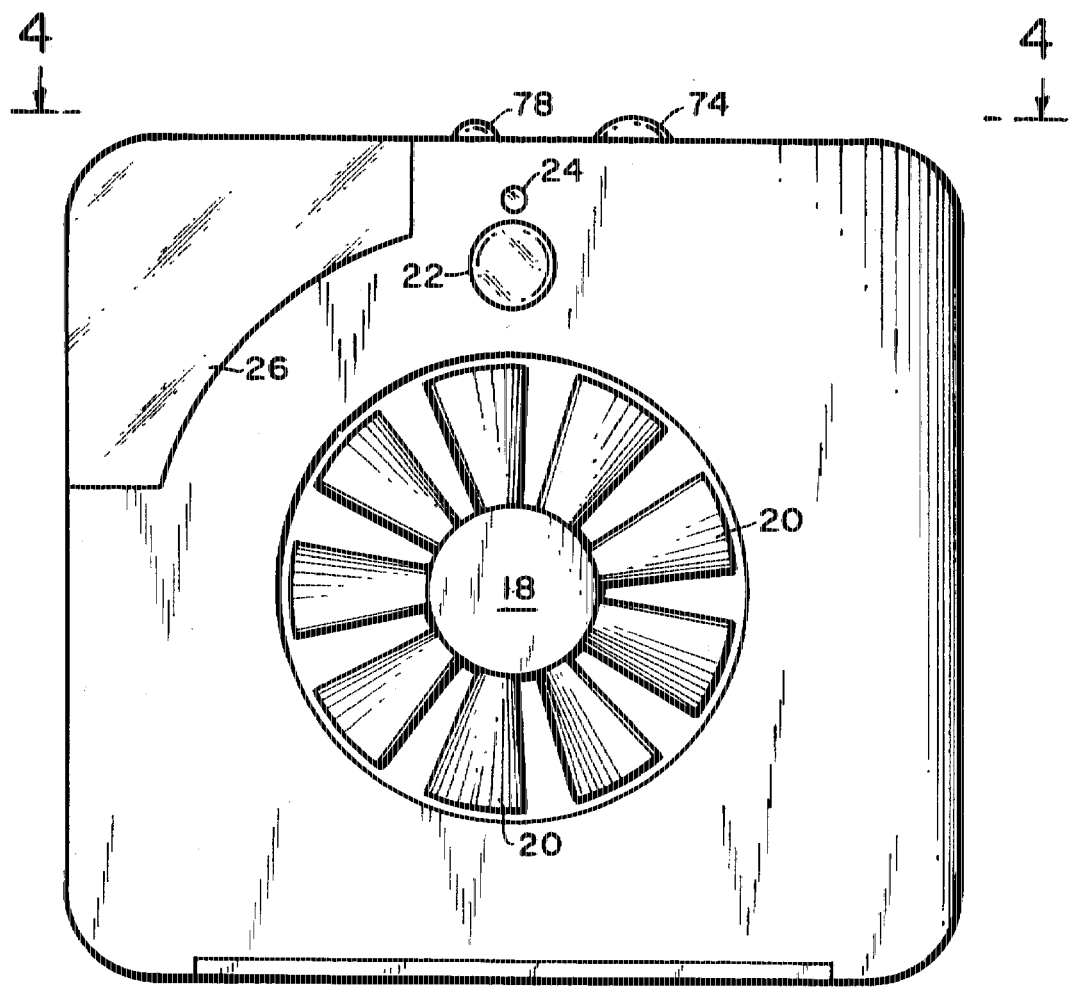
FIG. 3 is a front elevational view of the device.
Figure 4:
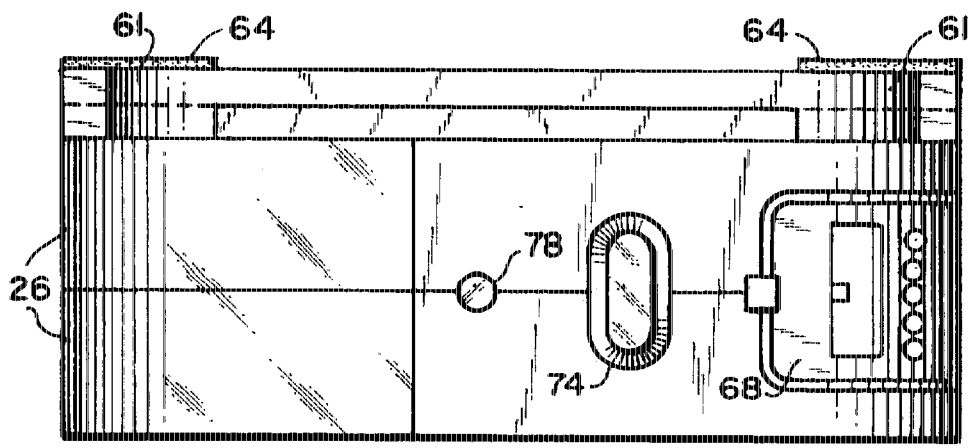
FIG. 4 is a view of the device taken along the lines 4—4 of FIG. 3.

The present invention is a portable, self-contained combination air freshener and air filter referred to by the reference numeral 10 and which can be self-supporting or mounted on a wall, for example in a bathroom or a kitchen. The air freshener and air filter is shown constructed in a rectangular configuration, but it is not intended to restrict the invention to any particular configuration. The housing 11 has a front wall 12 which is provided with an opening 14 having a protecting grille 16 behind which is a motor 18 with fan blade 20, as seen in FIG. 3. Located in the housing above the front opening 14 of the housing is a motion sensor 22 and a light sensor 24.

Figure 2:
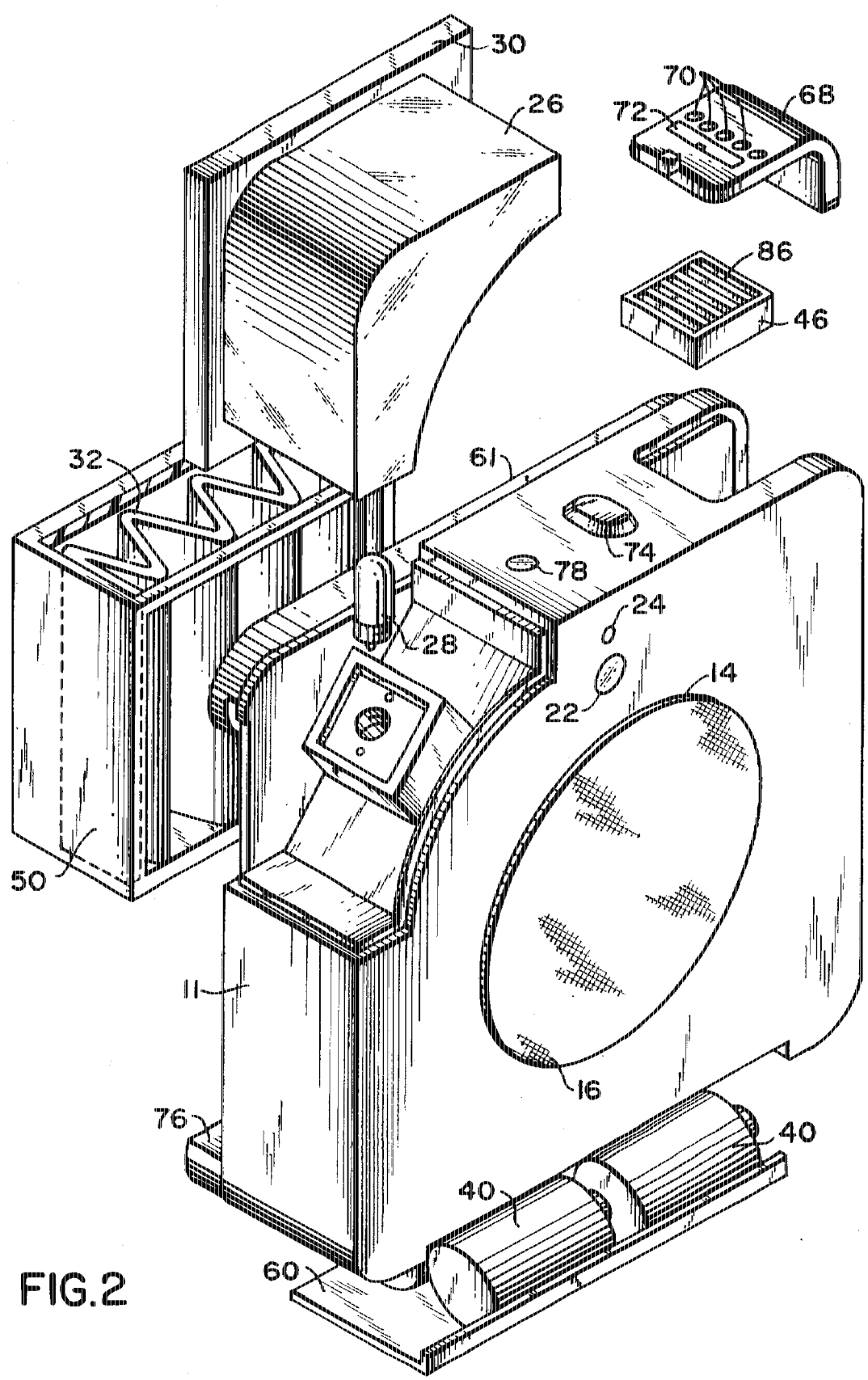
FIG. 2 is an exploded perspective view of my invention in the battery operated mode.

The upper left corner 26 of the housing 11 can be detached from the remainder of the housing, as seen in FIG. 2, in which a bulb 28 is located which functions as a night light since the corner 26 is fabricated of a light-transmitting material.

Figure 5:
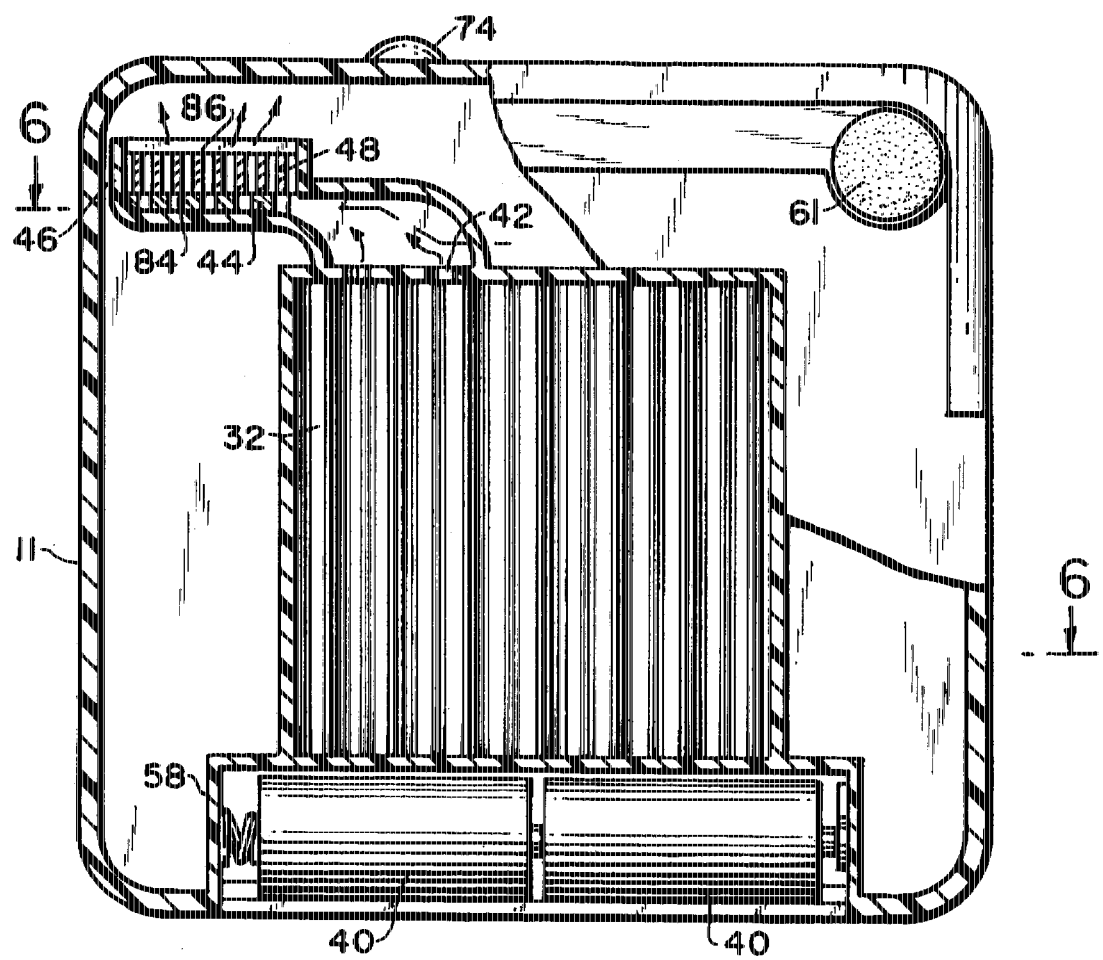
FIG. 5 is a rear sectional view of the device showing one of the filters and the diverted flow channel to the fragrance element.
Figure 6:
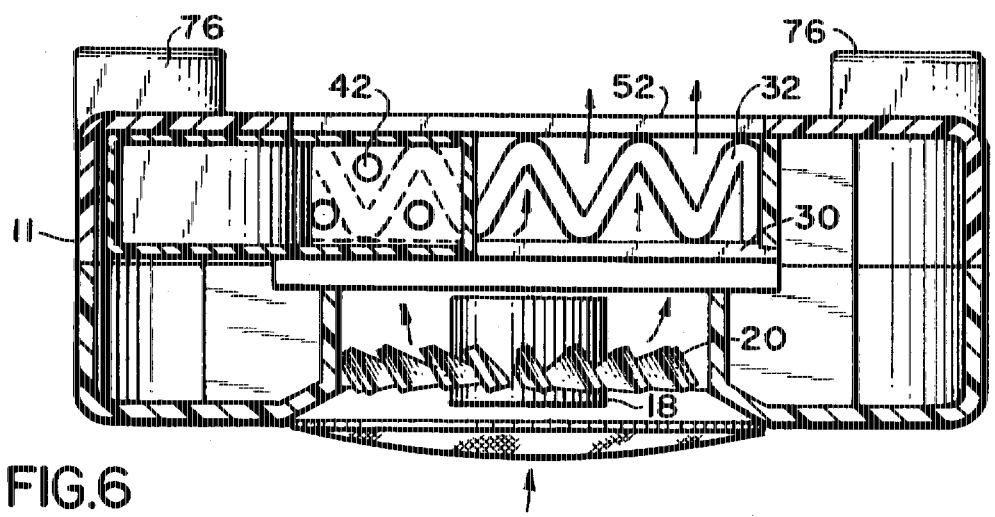
FIG. 6 is a view taken along the lines 6—6 of FIG. 5.

As seen in FIGS. 2, 5 and 6 directly behind the motor 18 and fan blades 20 are successive filter elements, such as foam filter 30 and charcoal and filtrate filter 32 in succession. It should be evident that the placement of the fan before the filter elements results in less load on the motor when the device is operative and is placed in a room for generating aroma, as well as filtering the room air.

Figure 1:
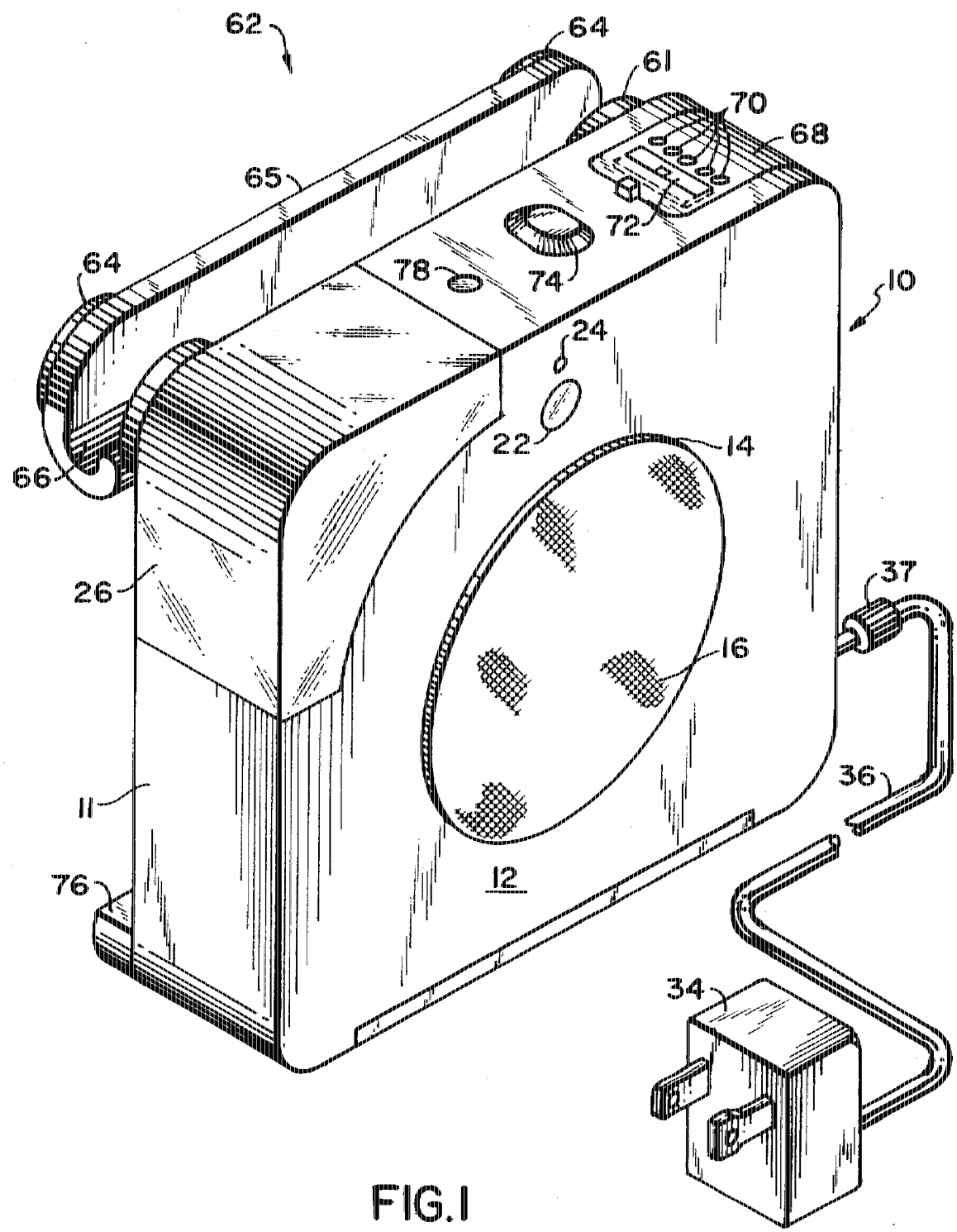
FIG. 1 is a perspective view of the combination air freshener and air leaner device constructed in accordance with the teachings of my invention in the AC operated mode.

As seen in FIGS. 1, 2 and 5 the present apparatus can be operated by either D.C. or A.C. power. In FIG. 1 the A.C. power source shows a plug 34 having a line cord 36 and a cylindrical plug 37 which is plugged into the inlet hole 38 in the housing the latter being shown in FIG. 9. In the alternative, D.C. operation of the device is by way of batteries 40, as seen in FIGS. 2 and 5.

Figure 7:
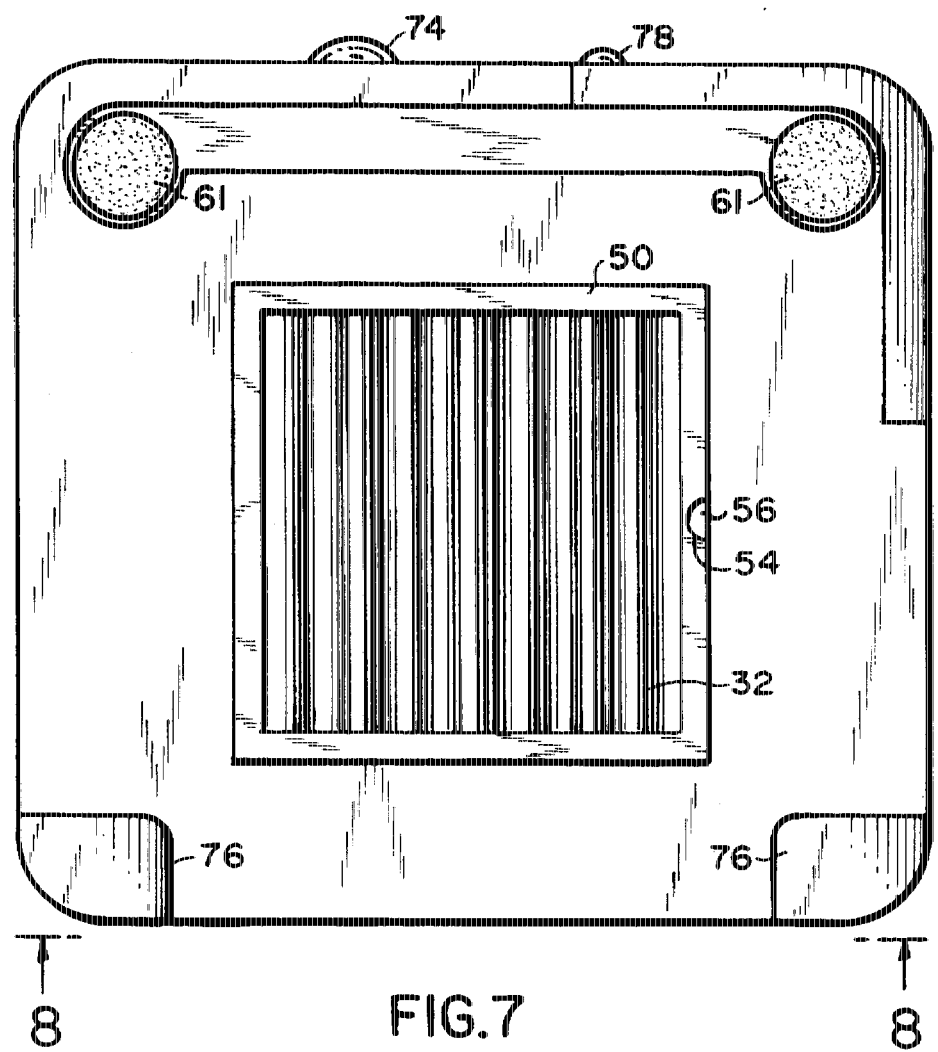
FIG. 7 is a rear view of the device.
Figure 8:
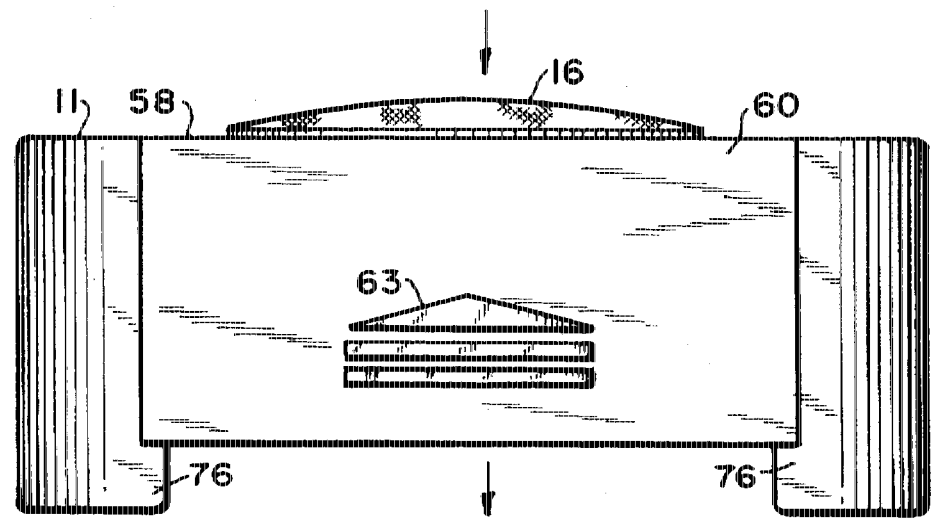
FIG. 8 is a bottom view taken along the lines 8—8 of FIG. 7.

Referring now to FIGS. 5 and 6, the path of the room air goes through the fan blades 20 and through the foam filter 30 and through the charcoal and filtrate filter 32 where part of the room air is diverted through openings 42 and into a conduit which conducts said part of the room air flow into openings 44 and into chamber 46 having scent material 48 therein. The charcoal and filtrate filter 32 is held in a plastic frame 50 whereas the foam filter 30 is fixed to the front of the plastic frame by means of adhesive or any other securing means. The filter 32 is an accordion form in order to present a larger surface area to the room air flow for more efficient filtering action. Thus, it should be apparent that the room air flow is filtered first and part of which is diverted to the scent chamber for generating aroma or scent while the remainder of the filtered air flow flows through the rear exit 52 of the housing. As seen in FIG. 7 the plastic frame 50 is provided with a notch 54 which is keyed with a correspondingly shaped projection 56 in housing 11. Battery compartment 58 is seen in FIGS. 5 and 8 for housing preferably four batteries 40. This compartment is open by sliding plate 60 in the direction of the arrow 63, as seen in FIG. 8. As seen in FIG. 7, the filter frame 50 can only be inserted in the back of the housing 11 in one way because of interlocking key elements 54 and 56 respectively. Consequently, this orientation insures that the air flow is not blocked by the filter 32 and part of the air flow seeks the holes or openings 42 for diverting part of the air flow to the scent container.

Figure 9:
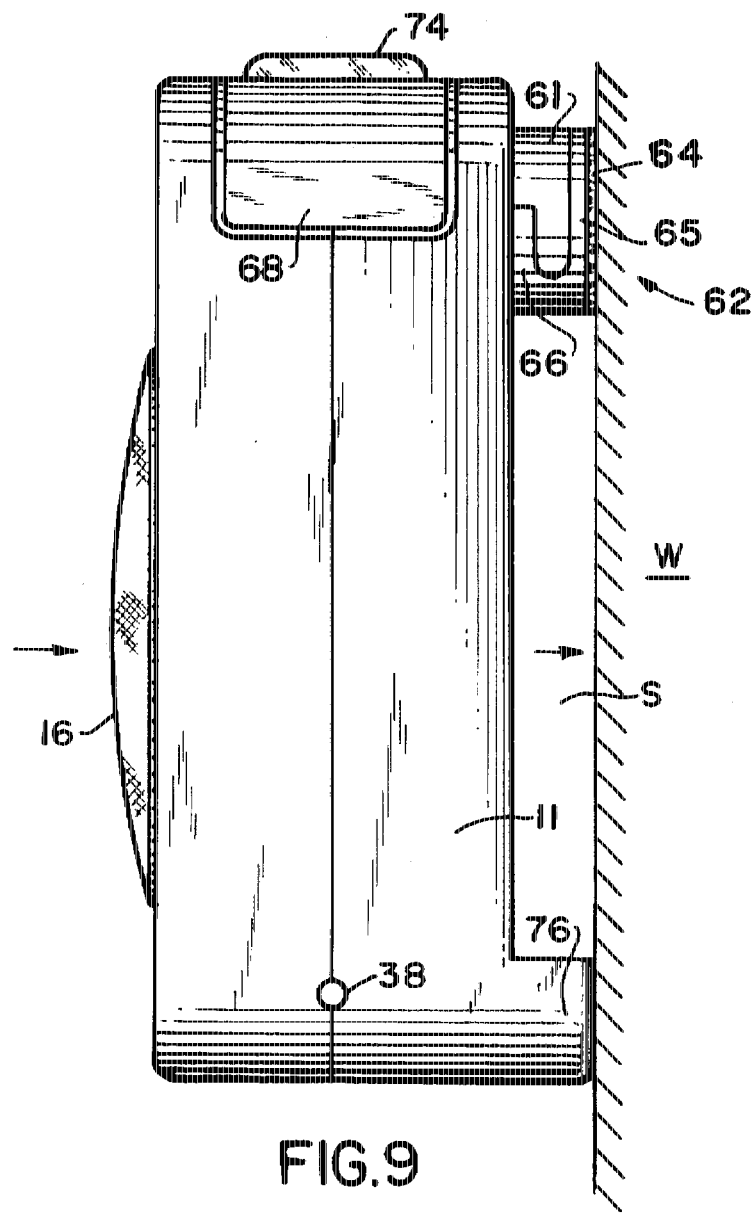
FIG. 9 is a side elevational view showing the device mounted on a wall and showing the path of air flow through the device.
Figure 10:
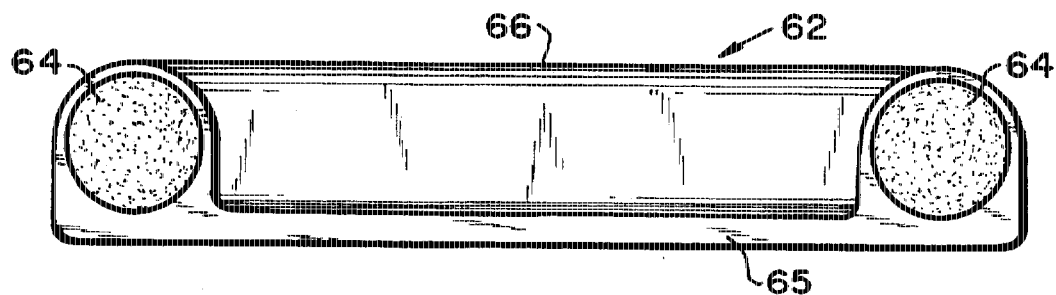
FIG. 10 is a rear elevational view of a wall hanger for the device.

The device or unit described herein can be self-supporting, or are affixed to a wall as shown in FIG. 9. In order to mount the device on a wall W and, as seen in FIGS. 1, 2 and 9, the rear of the housing 11 is provided with spaced hooks 61. A wall hanger referred to generally by the numeral 62 is shown having an adhesive on the back element 65 of the center portion 66 of the wall hanger, and is provided with circular parts which are spaced from the center portion 66. The circular parts 66 have cut-out recesses 64 into which the corresponding shaped curved hooks 61 on the housing interfits, as seen in FIG. 9. The hanger 62 may be affixed to the wall by means of screws or nails (not shown).

Scent container 46 having scent or aroma generating material 48 is provided with a cover 68 having a row of apertures or holes 70 for permitting the scent to rise therethrough and into the room. The amount of scent or aroma generated in a room can be adjusted by means of movement of a slide 72. The device is automatically operated by means of a motion sensor 22, however if one desires to operate the device manually the device is provided with a manual switch button 74. The night light bulb 28 is operated automatically by the light sensor 24 at the same time the motion detector senses a person entering the room. A timer (not shown) can deactivate the device and turn off the light bulb after a preselected time period. The night light bulb may also be operated or lit manually by means of the switch button 78 if the light sensor is inactive, but light is desired in the room. In that case the light bulb 28 functions as a flashlight.

FIG. 9 shows the combination air freshener and air filter device attached to a wall W. It should be evident that there is an open space S between the housing 11 and the wall W thus permitting the filter air to exit out the open filter frame 50 of the filter 32 and flow unimpeded into the room the device is located in. The space S is created by rearward projecting posts 76 at the bottom in the back of the housing and at the top in the back of the housing 11 fits into the hook 61 of the wall hanger thereby resulting in the back of the housing 11 standing off the wall W and forming the space S therebetween. The scent container 46 is provided with openings 84 in the bottom and openings 86 in the top of the container. A scent material 48 is placed in the container, or a material, such as cotton can be soaked or impregnated with a scent and placed within the container 46. As is apparent, an air flow will pass through opening 84 and through the scent material 48 and continues to flow out through the openings 86 as well as the holes 70 in the lid 68 of the chamber, and thereafter, as aroma will permeate the room the device is located in. The present invention therefore both filters the room air and flows a filtered air scent aroma into the room.

While the invention has been disclosed and described with reference to a single embodiment it will be apparent that changes and modifications may be made therein, and it is intended in the following claims to cover each such variation and modification as falls within the true spirit and scope of the present invention.

What is claimed is:

1. A combination portable self-contained automatic air freshener and air filter device for placement in a room comprising: a housing having a motor and rotating fan blades connected to said motor, at least one filter element in said housing and located downstream of said fan blades element, a first air exit in said housing located downstream of said fan blades and filter element, a first part of said room air being conducted through said filter element to produce filtered air, said filtered air being discharged out of said first exit in said housing to the room, an apertured receptacle in said housing, a fragrance element in said receptacle, a conduit for conducting another part of said room air in said housing through said conduit and said fragrance element and receptacle, a second air exit in said housing, said another part of said room air being discharged out of said second exit in said housing whereby aroma is generated in the room.

2. The device as claimed in claim 1 further comprising a heater juxtaposed to said fragrance element, and a motion sensor for operating said motor and fan blades, and activating the heater thereby emitting an aroma from said fragrance element into said room through said second air exit.

3. The device as claimed in claim 1 wherein one of said filter elements is constituted of a foam material.

4. The device as claimed in claim 1 wherein one of said filter elements is a charcoal filter.

5. The device as claimed in claim 1 wherein a power source is provided comprising at least one battery.

6. The device as claimed in claim 1 wherein a power source is provided comprising alternating current.

7. The device as claimed in claim 1 further comprising at least one hook projecting from the rear of said housing, and a wall hanger having end posts provided with means for attaching said posts to said housing, and said hook latching on said wall hanger for supporting said device but spaced from said wall.

8. The combination air cleaner and filter device as claimed in claim 7 wherein said housing is rectangular and provided with two posts located at the bottom two corners of said housing and wherein said hook is located at the top of the back of the housing.

9. The device as claimed in claim 7 wherein said means for attaching said posts to the wall is an adhesive material.

10. A combination portable self-contained automatic air freshener and air filter device for placement in a room comprising: a housing having a motor and rotating fan blades connected to said motor for drawing in atmospheric room air into said housing, at least two filter elements positioned downstream of said fan blades, a first air exit in the rear of said housing located downstream of said fan blades and filter elements, a first part of said room air being conducted through said filter elements producing filtered air, an apertured receptacle in said housing, a fragrance element in said receptacle, a second air exit, a conduit for conducting part of said filtered air through said fragrance element and out said second exit whereby aroma is generated in the room, means for conducting the remainder of said filtered air through said first exit in said housing to the room, and a plurality of spaced posts projecting from the rear of the housing whereby when said device is placed against a wall in said room a space is created between said wall and said first air exit to permit the filtered air in said device to be expelled from said housing unimpeded.

11. The device as claimed in claim 10 wherein one of said filter elements is constituted of foam material.

12. The device as claimed in claim 10 further providing a motion sensor for operating the device as soon as a person enters the room in which said device is located.

13. The device as claimed in claim 10 further providing a light sensor and a light bulb wherein skid light sensor activates said light bulb upon a person entering the room in which said device is located.

14. A combination portable self-contained automatic air freshener and air filter device for placement in a room comprising: a housing having a motor and rotating fan blades connected to said motor for drawing in atmospheric room air flow into said housing, two filter elements located behind and spaced from said fan blades, one of said filter elements being accordion shaped, at least one conduit in said housing, a first air exit located downstream of said fan blades and said filter elements whereby the filtered air flow is conducted through said first exit in the housing to the room, a receptacle in said housing, openings in both the bottom and top of said receptacle, a fragrance element in said receptacle, a second air exit whereby the remainder of the room air flow is conducted through said conduit, and through said fragrance element in said receptacle and out said second exit whereby aroma is generated in the room.

15. The device as claimed in claim 14 wherein said one of the filtering elements is a charcoal filter.

* * * * *